United States Patent
Masaki et al.

(10) Patent No.: US 11,926,062 B2
(45) Date of Patent: Mar. 12, 2024

(54) METHODS AND APPARATUS FOR CONTROLLING A CONTINUUM ROBOT

(71) Applicants: Canon U.S.A., Inc., Melville, NY (US); The Brigham and Women's Hospital Inc., Boston, MA (US)

(72) Inventors: Fumitaro Masaki, Cambridge, MA (US); Franklin King, Allston, MA (US); Nobuhiko Hata, Boston, MA (US); Takahisa Kato, Brookline, MA (US)

(73) Assignees: Canon U.S.A., Inc., Melville, NY (US); The Brigham and Women's Hospital, Inc., Boston, MA (US)

(*) Notice: Subject to any disclaimer, the term of this patent is extended or adjusted under 35 U.S.C. 154(b) by 597 days.

(21) Appl. No.: 17/175,484

(22) Filed: Feb. 12, 2021

(65) Prior Publication Data
US 2021/0260767 A1 Aug. 26, 2021

Related U.S. Application Data

(60) Provisional application No. 62/980,825, filed on Feb. 24, 2020.

(51) Int. Cl.
*B25J 9/16* (2006.01)
*A61B 1/00* (2006.01)
(Continued)

(52) U.S. Cl.
CPC ......... *B25J 9/1689* (2013.01); *A61B 1/00006* (2013.01); *A61B 1/00045* (2013.01);
(Continued)

(58) Field of Classification Search
CPC ........ B25J 9/1689; B25J 9/104; B25J 13/065; B25J 18/06; B25J 19/023; B25J 9/1625; A61B 1/00006; A61B 1/00045; A61B 1/00149; A61B 1/0052; A61B 1/267; A61B 10/04; A61B 2034/2051; A61B 2034/2059; A61B 2034/742; A61B 1/0051; A61B 1/2676; A61B 34/37; A61B 1/00087;
(Continued)

(56) References Cited

U.S. PATENT DOCUMENTS 8,423,115 B2 * 4/2013 Koblish ................. A61B 5/283
600/374
10,603,124 B2 * 3/2020 Camarillo ............. A61B 34/32
(Continued)

FOREIGN PATENT DOCUMENTS

| JP | H07328016 A | 12/1995 |
|---|---|---|
| JP | 2018171701 A | 11/2018 |
| JP | 2018175602 A | 11/2018 |

*Primary Examiner* — Ian Jen
*Assistant Examiner* — Renee LaRose
(74) *Attorney, Agent, or Firm* — Canon U.S.A., Inc. IP Division

(57) ABSTRACT

A continuum robot having at least two independently manipulateable bendable section for advancing the robot through a passage, without contacting fragile elements within the passage, wherein the robot incorporates control algorithms that enable the continuum robot to operate and advance into the passage, as well as the systems and procedures associated with the continuum robot and said functionality.

12 Claims, 4 Drawing Sheets

(51) Int. Cl.

| | |
|---|---|
| *A61B 1/005* | (2006.01) |
| *A61B 1/267* | (2006.01) |
| *A61B 10/04* | (2006.01) |
| *B25J 9/10* | (2006.01) |
| *B25J 13/06* | (2006.01) |
| *B25J 18/06* | (2006.01) |
| *B25J 19/02* | (2006.01) |

(52) U.S. Cl.
CPC ........ *A61B 1/00149* (2013.01); *A61B 1/0052* (2013.01); *A61B 1/267* (2013.01); *B25J 9/104* (2013.01); *B25J 13/065* (2013.01); *B25J 18/06* (2013.01); *B25J 19/023* (2013.01); *A61B 10/04* (2013.01)

(58) Field of Classification Search
CPC ..... A61B 1/05; A61B 2034/301; A61B 34/30; A61B 34/71; A61B 34/77; A61B 90/361; G05B 2219/40234
See application file for complete search history.

(56) References Cited

U.S. PATENT DOCUMENTS

| | | | |
|---|---|---|---|
| 10,967,504 B2 * | 4/2021 | Simaan | .................... B25J 9/161 |
| 2018/0296282 A1 | 10/2018 | Kose et al. | |

* cited by examiner

METHODS AND APPARATUS FOR CONTROLLING A CONTINUUM ROBOT

CROSS REFERENCE TO RELATED PATENT APPLICATIONS

This application claims priority from U.S. Provisional Patent Application No. 62/980,825 filed on Feb. 24, 2020, in the United States Patent and Trademark Office, the disclosure of which is incorporated herein in its entirety by reference.

FIELD OF THE DISCLOSURE

The present disclosure relates to methods and apparatus related to a control systems for a continuum robot. More particularly, the present disclosure is directed toward methods, systems and apparatus for a continuum robot configured with independently manipulateable bendable section for advancing the robot through a passage, without contacting fragile elements within the passage.

BACKGROUND OF THE DISCLOSURE

A continuum robot includes a plurality of bending sections having a flexible structure, wherein the shape of the continuum robot is controlled by deforming the bending sections. The robot mainly has two advantages over a robot including rigid links. The first advantage is that the continuum robot can move along a curve in a narrow space or in an environment with scattered objects in which the rigid link robot may get stuck. The second advantage is that it is possible to operate the continuum robot without damaging surrounding fragile elements because the continuum robot has intrinsic flexibility.

As such, the detection of an external force, which is required for the rigid link robot, is unnecessary. Taking advantages of these characteristics, it is expected that the continuum robot could be advantageously applied in the medical field, such as an endoscope sheath and a catheter, and to a robot for hazardous situations, such as a rescue robot. United States Patent Publication No. 2018/0296282 assigned to Canon, Inc. describes a control method for enabling a two-section continuum robot, which is used as an endoscope, for advancement into a space using follow-the-leader ("FTL") technology. In addition, the article "Robotic-Assisted Micro-Surgery for the Throat; the Trans-Nasal Approach" (2012/Simaan), details a two-section continuum robot with a camera manipulated by a user input device (see FIG. 5), wherein the direction of the user input device is mapped to the direction of the camera view.

However, with the methods taught in cited art, the posture and orientation of a single section continuum robot is defined using two variables in the coordinate system attached to the base of the bending section of the robot, bending angle $\theta$ and bending plane $\zeta$. The bending angle describes how much the robot bends from the straight posture, and the banding plane describes which direction the robot bends. If the robot has multiple bending sections, the coordinate systems are defined at the bases of each those corresponding bending sections. The posture of each bending section of the robot is defined by a pair of two variables defined in each coordinate system attached to the base of each section.

As a result, when the robot is operated inside the body, the operator obtains information mostly from the camera attached at the tip of the robot. From this camera view, pointing the robot to the desired direction, using the two variables (bending angle and plane) defined in the base coordinate system, is difficult due to lack of information in the relationship/orientation between the camera view and the coordinate system.

Furthermore, during biopsy, the endoscopic camera view is not sufficient to understand the spatial relationship between the tip of the endoscope and a lesion, which leads to experimental movements by the operator, which could be very harmful to the patient.

Accordingly, it would be particularly beneficial to devise methods, systems and apparatus which would allow for advancement of a medical device without contacting elements, all the while allowing for accurate identification of orientation and direction of travel, as well as other medical functions desirable in a medical diagnosis, probing or surgical setting.

SUMMARY

Thus, to address such exemplary needs in the industry, the presently disclosed apparatus teaches a robotic apparatus comprising: a continuum robot including at least one bending section having a proximal end, a distal end, and a centroid along a longitudinal direction of the continuum robot; an actuator configured to manipulate the at least one bending section; a controller configured to issue control command to the actuator; a control input device in communication with the controller, and configured to accept control input for bending of the distal end from an operator, wherein the distal end has an end-effector coordinate that has an origin at the center of the distal end and two-two axes perpendicular to a centroid of the continuum robot and one axis parallel to the centroid, wherein the proximal end has a robot base coordinate that has an origin at the center of the proximal end and two-two axes perpendicular to a centroid of the continuum robot and one axis parallel to the centroid, and wherein the controller is configured to: store a current distal orientation vector based on the robot base coordinate; read the control input from the control input device by a time interval; determine a bending input vector from the reading of the control input based on the end-effector coordinate; and issue the control command based on the current distal orientation vector, and the bending input vector by the time interval.

In additional embodiment, the robotic apparatus comprises a camera probe configured to provide an endoscopic view from the distal end of the at least one bending section, and to define a camera-view coordinate that includes an origin of the camera view coordinate at the center of the endoscopic view.

It is further contemplated that the subject innovation continuum robot maintains a relationship between the camera-view coordinate and the end-effector coordinate.

It is yet another embodiment wherein the control input generated by the operator is based on the endoscopic view provided by the camera probe.

In yet additional embodiments disclosed herein the robotic apparatus also includes a display configured to provide the endoscopic view from the camera probe.

In further embodiments, the robotic apparatus further comprises a view adjuster configured to rotate the endoscopic view on the display to adjust rotational orientation of the camera-view coordinate to the end-effector coordinate.

In another embodiment, the robotic apparatus controller is configured to generate a computer graphic symbol of the bending input vector, and superimpose the computer graphic symbol with the endoscopic view on the display.

In various embodiments, the robotic apparatus incorporates computer graphic symbols comprising an arrow/line symbol whose orientation signifies the orientation of the bending input vector and whose length signifies magnitude of the bending input vector by the time interval.

In other embodiment, the control input device comprises a joystick. In yet additional embodiments, the joystick is configured to accept the orientation of the bending input vector as tilting orientation, and the magnitude of the bending input vector as tilting angle.

In yet additional embodiments, the bending section is configured to bend by pushing or/and pulling at least two driving wires.

In additional embodiments, the controller is configured to calculate a next distal orientation by adding the bending input vector to the current distal orientation; and calculate pushing or/and pulling amount of the at least two driving wires based on a kinematic of the continuum robot to achieve the next distal orientation.

These and other objects, features, and advantages of the present disclosure will become apparent upon reading the following detailed description of exemplary embodiments of the present disclosure, when taken in conjunction with the appended drawings, and provided paragraphs.

BRIEF DESCRIPTION OF THE DRAWINGS

Further objects, features and advantages of the present invention will become apparent from the following detailed description when taken in conjunction with the accompanying figures showing illustrative embodiments of the present invention.

Figure 1A:
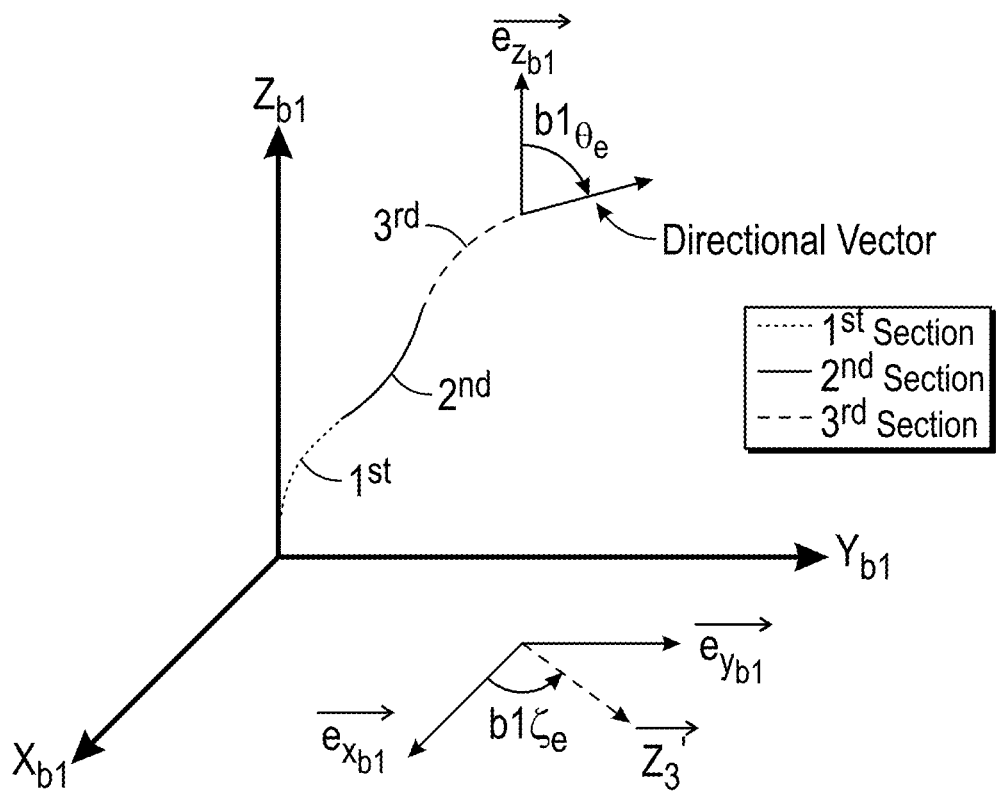
FIG. 1a illustrates a three-dimensional movement model of the subject continuum robot, according to one or more embodiment of the subject apparatus, method or system.
Figure 1B:
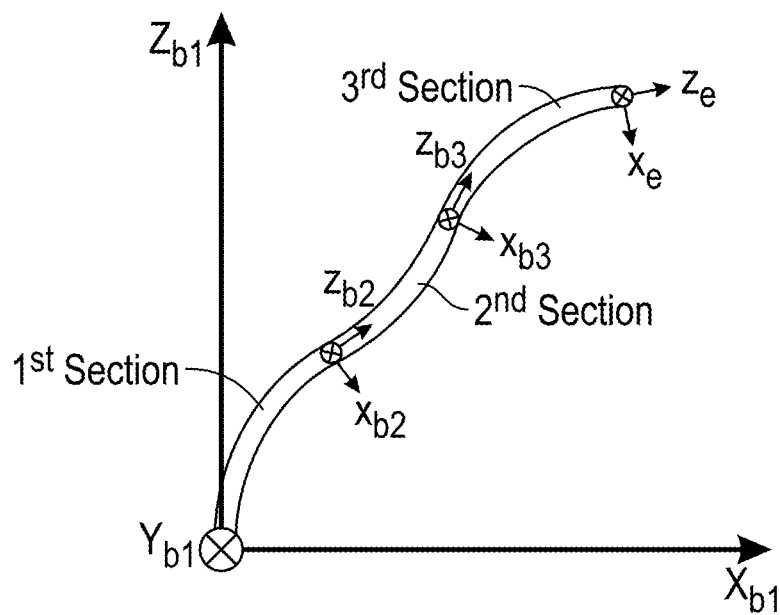
FIG. 1b shows a two-dimensional movement model of the subject continuum robot, according to one or more embodiment of the subject apparatus, method or system.

Throughout the Figures, the same reference numerals and characters, unless otherwise stated, are used to denote like features, elements, components or portions of the illustrated embodiments. In addition, reference numeral(s) including by the designation "'" (e.g. 12' or 24') signify secondary elements and/or references of the same nature and/or kind. Moreover, while the subject disclosure will now be described in detail with reference to the Figures, it is done so in connection with the illustrative embodiments. It is intended that changes and modifications can be made to the described embodiments without departing from the true scope and spirit of the subject disclosure as defined by the appended paragraphs.

DETAILED DESCRIPTION OF THE DISCLOSURE

In the subject disclosure, Applicant will first identify the nomenclature of the symbols provided in the Figures and accompanying calculations and algorithms that enable the continuum robot to operate and advance into a path. As such:

$^A x$: x defined in {A} coordinate system;

$^A R_{B,i}$: Rotation matrix of coordinate system {B} relative to {A} at i-th attempt;

e: end-effector coordinate system;

bj base-coordinate system at the base of the j-th section of the robot (j=1: most proximal section of the robot);

$^A p_i$: directional vector of the tip of the robot defined in {A} coordinate system at the i-th attempt $^A \theta_i$: bending angle where angle between $z_A$ axis and directional vector of the tip of the robot defined in {A} coordinate system at the i-th attempt; and $^A \zeta_i$: bending plane where angle between $x_A$ axis and directional vector of the tip of the robot projected onto $x_A$-$y_A$ plane defined in {A} coordinate system at the i-th attempt.

First-Person Control

According to the subject innovation, tendon-driven three-section robots with an endoscopic camera at the tip of the robot are used to identify and/or diagnose various elements during medical procedures, like for instance, a lung nodule. The direction of the camera view in the endoscope matches the end-effector coordinate system, which can be seen in FIG. 2. The end-effector coordinate system is mapped to the direction of a controller (e.g. joystick) which controls the robot via an operator. The operator operates the tip of the robot in the end-effector coordinate system (referred to as "First-Person Control"), wherein the joystick control is fully applicable in a 360 degree fashion, allowing a wide range of manipulation of the robot.

When the operator tries to point the robot to the next airway (FIG. 2), the operator tilts the joystick. The amount and direction the joystick is tilted decides the amount of desired velocity (direction and speed) of the bending of the tip of the robot, ($^e \theta_{i+1}$), defined in the end-effector coordinate system and the direction of the joystick decides desired bending plane of the tip of the robot, ($^e \zeta_{i+1}$), defined in the end-effector coordinate system.

Then ($^e \theta_{i+1}$, $^e \zeta_{i+1}$) is converted to ($^{b1} \theta_{i+1}$, $^{b1} \zeta_{i+1}$), and stored in the memory of the apparatus.

Then ($^e \theta_{i+1}$, $^e \zeta_{i+1}$) is converted to ($^{b1} \theta_{i+1}$, $^{b1} \zeta_{i+1}$) using the directional vector $p_{i+1}$ and rotation matrix $^e R_{b1,i}$ and stored in the memory of the apparatus as follows:

$$^{b1} p_{i+1} = {}^e R_{b1,i} \, {}^e p_{i+1}$$

Here, b1 coordinate system is the coordinate system attached to the base of the $1^{st}$ section, i.e. the coordinate system attached to the base of the entire robot (robot-base coordinate system). The amount of tendons pulled/pushed is computed from ($^{b1} \theta_{i+1}$, $^{b1} \zeta_{i+1}$). Note that once ($^{b1} \theta_{i+1}$, $^{b1} \zeta_{i+1}$) are derived, the amount of tendons pulled/pushed is computed without any dependence on the posture of other sections. The tendons are pulled/pushed based on the computed amount, and the robot is bent toward the desired direction.

Figure 2:
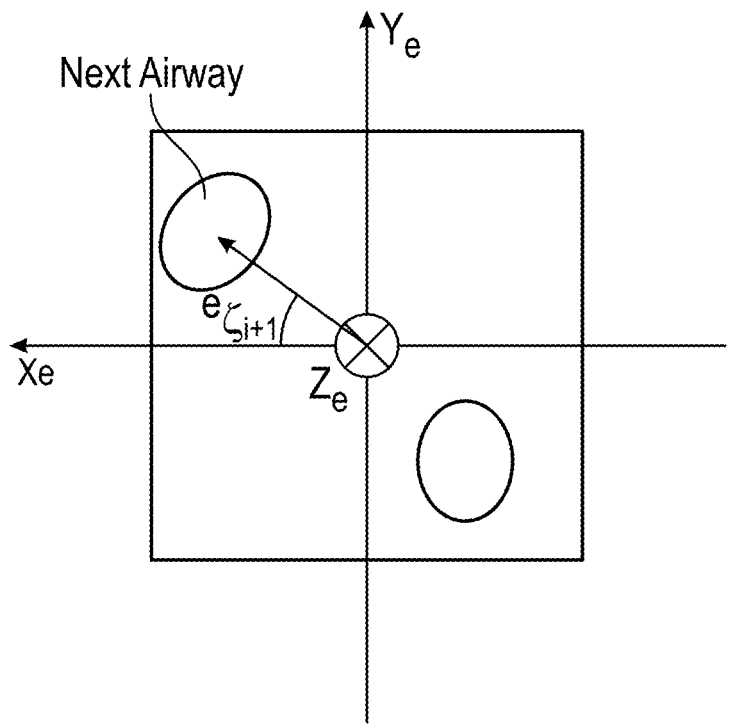
FIG. 2 provides an exemplary camera view from the subject continuum robot, according to one or more embodiment of the subject apparatus, method or system.
Figure 3A:
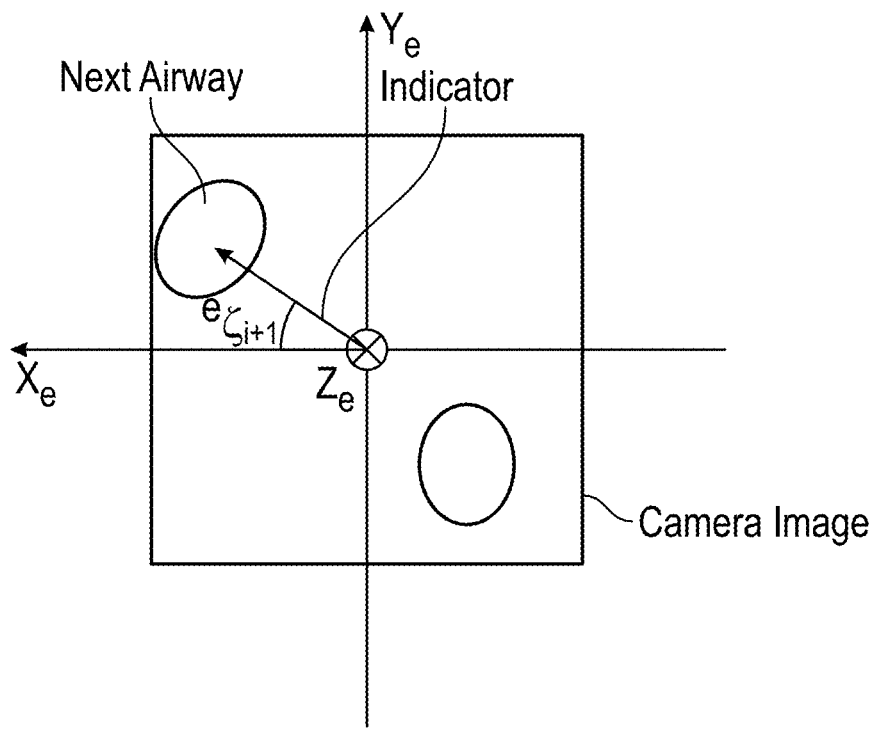
FIGS. 3a, 3b, and 3c provide exemplary camera views from the subject continuum robot as the robot is adjusted for proper orientation, according to one or more embodiment of the subject apparatus, method or system.
Figure 3B:
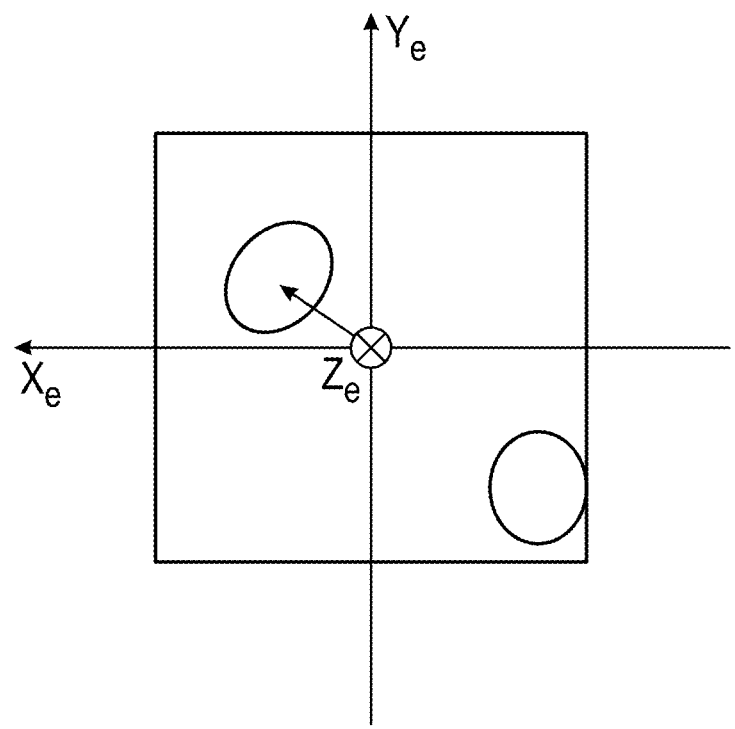
Figure 3C:
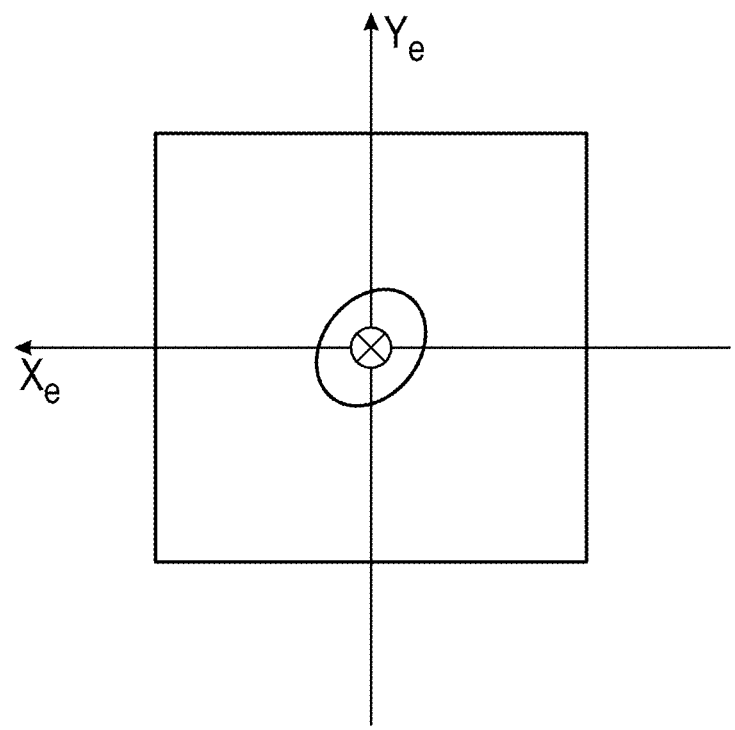

Because the camera view doesn't have depth information, deciding ($^e \theta_{i+1}$) as the exact angle toward the next airway is difficult. In this embodiment, the operator sets the maximal increment value of ($^e \theta_{i+1}$) as the maximal tilting of the joystick and repeats aforementioned steps until the robot turns to the next airway, i.e, the next airway comes to the center of the camera view (FIG. 3). The operator can select the increment value of ($^e\theta_{i+1}$) by adjusting the tilting amount of the joystick during operation. As shown in FIG. 2, an arrow is overlaid over the camera view. The size and direction of the arrow indicate ($^e\theta_{i+1}$, $^e\zeta_{i+1}$). If the operator is well trained, the operator can set a larger increment value of $^e\theta_{i+1}$ through a dialog box in the GUI. The aforementioned series of repeated steps (visual feedback loop via the operator) is useful especially in the tortuous pathway where it applies unexpected force to the robot and deforms it.

Accordingly, even if the motion of the robot is inaccurate, due to unexpected force, the adjustable incremental value and trial-and-error steps by the operator eventually point the robot toward the correct direction for the next airway. If the increment value is not small enough, the operator can set a new value through a dialog box in GUI. This can be automated based on the tortuosity of the airway, defined as the shape of the airway, such as the total angle of bifurcation points.

The incremental value can be also automatically set using other information. As the robot advances deeper in the lung, the diameter of the airway becomes smaller. This requires finer control of the robot. Therefore, the increment value is automatically set based on how deep the robot advances into the lung, or the number of striations of the airway.
Follow-The-Leader ("FTL")

The first and second sections may be controlled by Follow-The-Leader motion control. When the first and second sections pass through a bifurcation where the third section has already passed, the history of ($^{b1}\theta_3$, $^{b1}\zeta_3$) used for the third section is applied to other sections.
Sampling When the robot reaches the target lesion, the operator collects the tissue sample using a biopsy tools. The operator may collect multiple tissue samples at various locations of the lesion.

Embodiment 2

In this iteration of the subject innovation, the endoscopic camera is substituted for a 6 Degree of Freedom (DOF) Electro-Magnetic (EM) tracking sensor. By registering the position of EM tracking sensor onto a CT image of the lung taken before the bronchoscopy, an operator obtains virtual camera view. Similar to the camera view taken by an actual endoscopic camera described in Embodiment 1, the direction of the virtual camera view matches with the end-effector coordinate system. The end-effector coordinate system is mapped to the direction of the joystick allowing the operator to operate the tip of the robot in the end-effector coordinate system (First-Person Control).

The combination of EM tracking sensor and the CT image gives the operator the current position of the EM tracking sensor in the CT image and the path to the target lesion.

Figure 4:
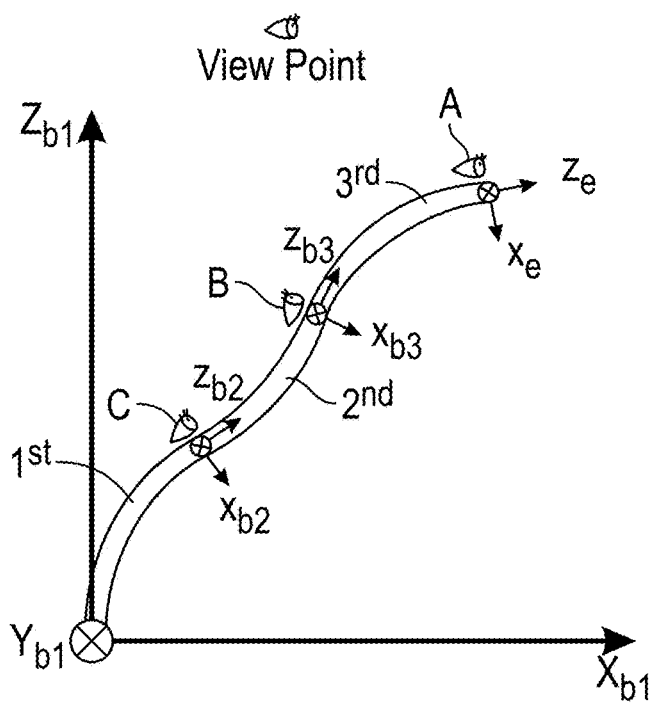
FIG. 4 illustrates an exemplary movement model of the subject continuum robot, according to one or more embodiment of the subject apparatus, method or system.
Figure 5:
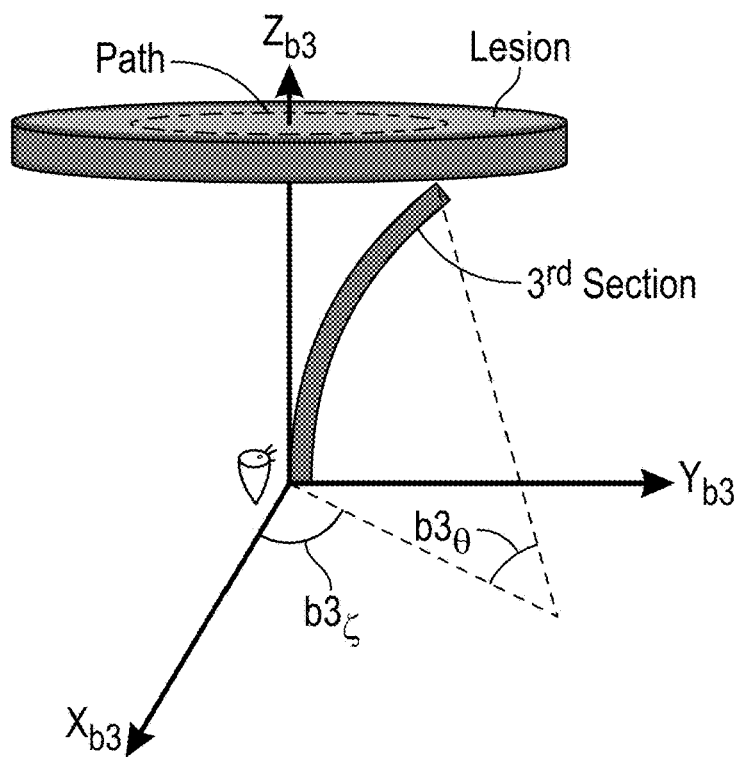
FIG. 5 provides a graph of an alternative camera view of the subject continuum robot, according to one or more embodiment of the subject apparatus, method or system.

By using virtual camera view, the operator can select his/her virtual viewpoint. During navigation toward the lesion, the operator controls the tip of the robot in the end-effector coordinate system. When the robot reaches the target lesion, the operator switches his/her viewpoint from the tip of the robot (end-effector coordinate system (viewpoint A in FIG. 4)) to the base of the 3$^{rd}$ section (b3 coordinate system (viewpoint B in FIG. 4)), by pushing a switching button in GUI. Using viewpoint B, set at the b3 coordinate system, the operator can virtually view both of the entire body of the 3$^{rd}$ section and the target lesion (FIG. 5) depicted in the virtual image based on CT data. When the operator pushes the button to switch to viewpoint B, set at the b3 coordinate system, the b3 coordinate system is mapped to the direction of the joystick. This is useful to collect samples along a concentric path on the lesion (dash line in FIG. 5) because the user can achieve this path by just rotating the joystick (i.e. fix the $^{b3}\theta_{i+1}$, and change $^{b3}\zeta_{i+1}$).

Similar to Embodiment 1, ($^{b3}\theta_{i+1}$, $^{b3}\zeta_{i+1}$) are converted to ($^{b1}\theta_{i+1}$, $^{b1}\zeta_{i+1}$) using the directional vector $p_{i+1}$ and the rotation matrix $^{b3}R_{b1,i}$.

$$^{b1}p_{i+1} = {}^{b3}R_{b1,i} \, {}^{b3}p_{i+1}$$

Then, the amount of tendons pulled/pushed is computed from ($^{b1}\theta_{i+1}$, $^{b1}\zeta_{i+1}$). The tendons are pulled/pushed based on the computed amount, and the robot is bent toward the desired direction to collect the tissue.

Not limited to switching from the end-effector coordinate system to the b3 coordinate system, the operator can select the viewpoint based on his/her objective. When the operator selects a viewpoint, the coordinate system is automatically mapped to the direction of the game joystick.

The invention claimed is:

1. A robotic apparatus comprising:
   continuum robot including at least one bending section having a proximal end, a distal end, and a centroid along a longitudinal direction of the continuum robot;
   an actuator configured to manipulate the at least one bending section;
   a controller configured to issue control command to the actuator;
   a control input device in communication with the controller, and configured to accept control input for bending of the distal end from an operator,
   wherein the distal end has an end-effector coordinate that has an origin at the center of the distal end and two axes perpendicular to a centroid of the continuum robot and one axis parallel to the centroid,
   wherein the proximal end has a robot base coordinate that has an origin at the center of the proximal end and two-two axes perpendicular to a centroid of the continuum robot and one axis parallel to the centroid, and
   wherein the controller is configured to:
   store a current distal orientation vector based on the robot base coordinate,
   read the control input from the control input device by a time interval,
   determine a bending input vector from the reading of the control input based on the end-effector coordinate, and
   issue the control command based on the current distal orientation vector, and the bending input vector by the time interval.

2. The robotic apparatus according to claim 1, further comprising:
   a camera probe configured to provide an endoscopic view from the distal end of the at least one bending section, and to define a camera-view coordinate that includes an origin of the camera view coordinate at the center of the endoscopic view.

3. The robotic apparatus of claim 2, further comprising:
   A display configured to provide the endoscopic view from the camera probe.

4. The robotic apparatus of claim 2, wherein the continuum robot maintains a relationship between the camera-view coordinate and the end-effector coordinate.

5. The robotic apparatus of claim 2, wherein the control input generated by the operator is based on the endoscopic view provided by the camera probe.

6. The robotic apparatus according to claim 2, further comprising:
   a view adjuster configured to rotate the endoscopic view on the display to adjust rotational orientation of the camera-view coordinate to the end-effector coordinate.

7. The robotic apparatus according to claim 2, wherein the controller is configured to generate a computer graphic symbol of the bending input vector, and superimpose the computer graphic symbol with the endoscopic view on the display.

8. The robotic apparatus according to claim 7, wherein the computer graphic symbol comprises an arrow/line symbol whose orientation signifies the orientation of the bending input vector and whose length signifies magnitude of the bending input vector by the time interval.

9. The robotic apparatus according to claim 8, wherein the control input device comprises a joystick.

10. The robotic apparatus according to claim 9, wherein the joystick is configured to accept the orientation of the bending input vector as tilting orientation, and the magnitude of the bending input vector as tilting angle.

11. The robotic apparatus according to claim 1, wherein the bending section is configured to bend by pushing or/and pulling at least two driving wires.

12. The robotic apparatus according to claim 11, wherein the controller is configured to:
   calculate a next distal orientation by adding the bending input vector to the current distal orientation; and
   calculate pushing or/and pulling amount of the at least two driving wires based on a kinematic of the continuum robot to achieve the next distal orientation.

\* \* \* \* \*